(12) United States Patent
McAleavy et al.

(10) Patent No.: US 11,286,076 B2
(45) Date of Patent: Mar. 29, 2022

(54) CONTAINED TRANSFER OF STERILE OR ASEPTIC MATERIALS

(71) Applicant: Ezi-Dock Systems Limited, Kirby-in-Ashfield (GB)

(72) Inventors: Stephen Thomas McAleavy, Doncaster (GB); Michael Ronald Brimson, Selston (GB)

(73) Assignee: Ezi-Dock Systems Limited, Kirkby-in-Ashfield (GB)

( * ) Notice: Subject to any disclaimer, the term of this patent is extended or adjusted under 35 U.S.C. 154(b) by 70 days.

(21) Appl. No.: 16/488,476

(22) PCT Filed: Feb. 23, 2018

(86) PCT No.: PCT/GB2018/050483
§ 371 (c)(1),
(2) Date: Aug. 23, 2019

(87) PCT Pub. No.: WO2018/154321
PCT Pub. Date: Aug. 30, 2018

(65) Prior Publication Data
US 2020/0031512 A1     Jan. 30, 2020

(30) Foreign Application Priority Data
Feb. 23, 2017    (GB) ..................................... 1702910

(51) Int. Cl.
*B65B 69/00* (2006.01)
*B65B 39/00* (2006.01)
(Continued)

(52) U.S. Cl.
CPC ............ *B65B 69/0075* (2013.01); *A61L 2/10* (2013.01); *B65B 39/001* (2013.01);
(Continued)

(58) Field of Classification Search
CPC . B65B 39/001; B65B 39/005; B65B 69/0075; B65B 2210/06; B65B 2210/08; B65G 69/183
(Continued)

(56) References Cited

U.S. PATENT DOCUMENTS 5,490,546 A    2/1996  Lhoest
6,030,578 A *  2/2000  McDonald ................ A61L 2/10
                                                    422/24
(Continued)

FOREIGN PATENT DOCUMENTS

DE    19617467 A1 * 11/1997  ............... A61L 2/10
EP     0 800 480 B1    4/1999
WO    2011/007170 A2   1/2011

OTHER PUBLICATIONS

International Search Report and Written Opinion dated Apr. 16, 2018, issued in corresponding International Application No. PCT/GB2018/050483, filed Feb. 23, 2018, 12 pages.

*Primary Examiner* — Stephen F. Gerrity
(74) *Attorney, Agent, or Firm* — Christensen O'Connor Johnson Kindness PLLC

(57) ABSTRACT

A system for contained sterile/aseptic transfer of materials comprises a coupler assembly (6) including an active valve assembly (9) having an active valve and docking part and a passive valve assembly (7) which comprises a passive valve and a complimentary docking part, the two docking parts enabling the two valve assemblies to be secured together in a first position with a void formed between the two facing surfaces of the closed valves. A sterilisation device (20) including a UV emitter assembly is arranged to emit UV light into the void such that the exposed outer surfaces of at least the passive valve and active valve are exposed to UV light emitted by the emitter assembly after the two docking parts are secured together in the first position, and prior to
(Continued)

moving of the passive/active valve to a second position where material may transfer through the opened valves.

15 Claims, 14 Drawing Sheets

(51) Int. Cl.
  *B65G 69/18* (2006.01)
  *A61L 2/10* (2006.01)
(52) U.S. Cl.
  CPC .......... *B65B 39/005* (2013.01); *B65G 69/183* (2013.01); *A61L 2202/11* (2013.01); *B65B 2210/06* (2013.01); *B65B 2210/08* (2013.01)
(58) Field of Classification Search
  USPC .......................................................... 141/85
  See application file for complete search history.

(56) References Cited

U.S. PATENT DOCUMENTS

| | | | |
|---|---|---|---|
| 6,307,206 B1 * | 10/2001 | Riviere et al. ........... | B25J 21/02 250/453.11 |
| 6,308,749 B1 | 10/2001 | Brossard et al. | |
| 6,849,233 B2 * | 2/2005 | Bushnell et al. ......... | A61L 2/10 422/24 |
| 6,897,452 B2 * | 5/2005 | McDonald et al. ...... | A61L 2/10 422/24 |
| 6,940,075 B2 * | 9/2005 | Schulz ................... | C02F 1/325 422/186.3 |
| 8,410,453 B2 * | 4/2013 | Lee et al. .................. | A61L 2/10 422/24 |
| 8,894,925 B2 * | 11/2014 | Parfitt et al. .............. | A61L 2/10 422/24 |
| 9,079,726 B2 * | 7/2015 | Brimson et al. .... | B65B 69/0075 |
| 2014/0356229 A1 * | 12/2014 | Farren ...................... | A61L 2/10 422/24 |

* cited by examiner

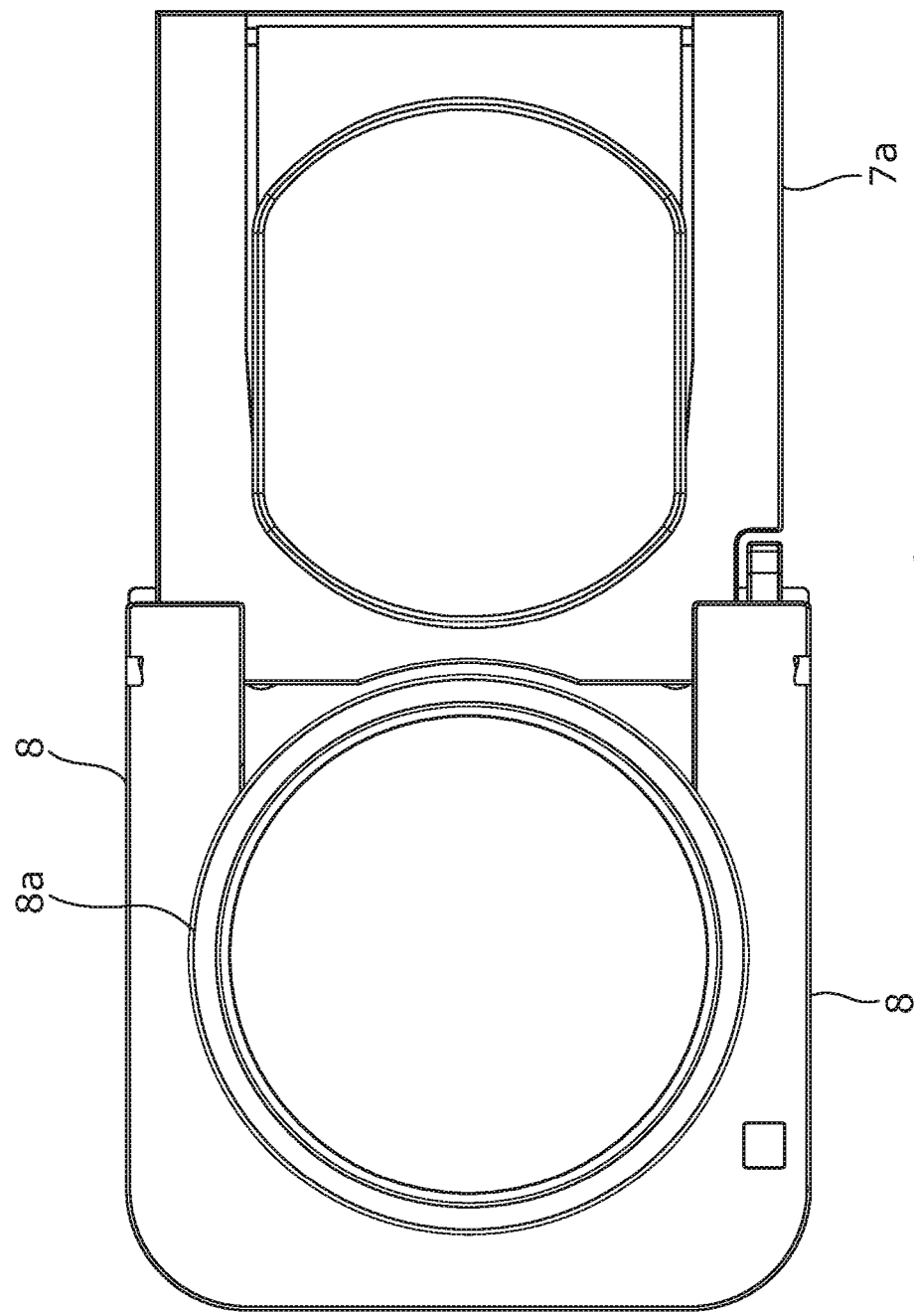

CONTAINED TRANSFER OF STERILE OR ASEPTIC MATERIALS

This invention relates to a coupler assembly for use in controlling the flow of a materials that are sterile, or require handling or processing in a sterile/aseptic environment, such as a pharmaceutical powders/tablets/capsules or items used in conjunction with the storage or delivery of such products i.e. stoppers or vials, into or out from a container such as a flexible bag or a bottle. It is especially suited to controlling the flow of powdered material but may also be used with granules, flakes, pastes (wet cake), crystals or perhaps fluids. It also relates to a system for sterilising one or more parts of a coupling assembly.

There is often difficulty when connecting the containers to apparatus for filling or emptying them. In particular, it is desirable to create a tight seal to limit contamination of the contents from the environment, and likewise to limit the escape of the contents into the environment during the filling or emptying operation. It may also be desirable to avoid escape of the contents when disconnecting the containers from such apparatus.

One way to create a tight seal is to weld a single ring around the opening of the container. This ring then forms a rigid connector which can be attached to a filling and or emptying apparatus. However, it is difficult and time consuming to achieve an accurate welded fitting of a single ring, and welding may not be suitable for all container materials.

An alternative is proposed in the applicant's earlier UK patent application GB 2 412 652 A in which a connection assembly with a multipart construction is presented, allowing simple attachment of the connection assembly to the container.

In the pharmaceutical industry expensive and potentially health hazardous powders or granules need to be transferred into various powder processing machinery. It is essential that these types of materials are contained within the processing system for obvious health reasons and that they are not wasted by becoming trapped on obstructions. When powders are transferred into processing equipment often bags containing the powder are docked onto one another using a coupler assembly. The most common coupler assembly is known as a split butterfly valve which allows the bag and the processing unit to be separately isolated. A split butterfly valve comprises two valves that cannot be operated independently and must be connected together in the middle to allow them to rotate and function. One part, called the passive, is permanently coupled to the bag, and another, known as the active, can be connected to a receptacle into which the contents of the bag are to be discharged. The two valves allows the bag and the unit to be separately isolated reducing the risk of powder escaping either from the bag or back flowing out of the processing equipment.

The passive part of a split butterfly valve can be very heavy and can cause problems when working in conjunction with flexible polyethylene charge bags. Another problem is the release of powder which can occur due to product hang up on the outer edge of the split butterfly diaphragm and side gasket areas.

In an alternative, in the applicant's earlier European patent EP2454158 a coupler assembly is described having two slide valves rather than butterfly valves. The assembly comprises an active valve assembly having an active valve and docking part and a passive valve assembly which comprises a passive valve and a complimentary docking part, the two docking parts enabling the two assemblies to be secured together such that both the passive valve and active valve can be opened to provide a passage for powder through both valves. The coupler assembly further includes a spigot movable between a first position in which it allows the active valve to close with the spigot on the opposite side of the active valve to the docking part which engages the passive valve assembly, and a second position in which the active valve is held in an open position and the spigot provides a passage for material passing through the passive valve to flow through the active valve whilst substantially preventing exposure of at least part of the active valve to any of the flowing material. Once the spigot has passed through the open active valve to protect it from contamination, the passive valve can be opened so that the materials in the bag can safely discharge through the spigot.

After discharge, the passive valve is closed and the spigot pulled back through the active valve which is then closed. This arrangement ensures there is no contact of material that is discharged with the outer face of the active valve, i.e. the face open to atmosphere when the bag is decoupled.

The applicant has appreciated that further improvements can be made to coupler assemblies where an even higher degree of cleanliness to ensure there is no contamination is required.

According to a first aspect the invention provides a system for contained sterile/aseptic transfer of materials comprising a coupler assembly including an active valve assembly having an active valve and docking part and a passive valve assembly which comprises a passive valve and a complimentary docking part, the two docking parts enabling the two valve assemblies to be secured together in a first position with a void formed between the two facing surfaces of the closed valves, and characterised by further including a sterilisation device including a UV emitter assembly arranged in use to emitting UV light into the void such that the exposed outer surfaces of at least the passive valve and active valve are exposed to UV light emitted by the emitter assembly after the two docking parts are secured together in the first position, and prior to moving of the passive/active valve to a second position where material may transfer through the opened valves.

The two docking parts may be arranged such that the void between the two valve surfaces is sealed around a periphery by the docking parts.

The two valves, in the first position, may be arranged such that they cannot be opened, requiring movement of at least one of the valves to an intermediate position before they can be moved to the second position.

The valves may comprise slide valves and the movement between the first position and second position may comprise movement in a direction orthogonal to the plane of the slide valves.

The UV emitter assembly may be located within, adjacent or at least partially within the void formed by the passive and active docking parts.

The UV-C emitter assembly may be located in a space that at least partially surrounds the void formed between the passive valve assembly and the active valve assembly.

The UV-C emitter assembly may comprise a surround which extends at least partially, and preferably all the way, around the opening that is covered by the two valves when closed. The surround therefore does not impede the flow of material when the valves are opened.

The surround may comprise four perimeter walls surrounding the opening.

The surround may form part of a seal that seals the perimeter of the void to prevent UV-C radiation escaping from the connector assembly. Alternatively a separate seal may be provided that surrounds the perimeter of the void and encloses the UV-C emitter.

The UV emitter assembly of the sterilisation device may be an integral part of the docking part of the active valve assembly or may be removable from the active valve assembly. It may be an integral part of the passive valve docking part or removable from the passive valve assembly. It may comprise a discrete component that in use is releasably sandwiched between the active and passive valve assemblies. It may form a seal between the two valve assemblies, or may be surrounded by a seal.

Providing a UV-C sterilisation device which can be located in the void formed between the active and passive valve assemblies during an initial docking stage enables the exposed outer faces of the passive valve to be sterilised prior to discharge using UV-C light. This provides a convenient and highly effective arrangement for removing any germs/bacteria that may be on the passive valve that could otherwise contaminate the coupler assembly or pass with the discharge material.

The UV-C emitter assembly and the docking parts may be configured such that when docked and prior to opening the passive valve the passive valve is sealed from the external environment. Thus, once sterilised by exposure to UV-C light from the emitter assembly no recontamination can occur until undocking of the assemblies. They may remain sealed upon movement to the second position.

The UV-C emitter assembly may comprise at least one, but preferably a plurality of UV-C light emitting devices that in use emit UV light into the void.

The light emitting devices may be spaced around the surround.

The UV light emitter assembly of the sterilisation device may be an integral part of the docking part of the active valve assembly or may be removable from the active valve assembly. It may be an integral part of the passive valve docking part or removable from the passive valve assembly. It may comprise a discrete component that in use is releasably sandwiched between the active and passive valve assemblies. It may form a seal between the two valve assemblies, or may be surrounded by a seal.

The UV light emitting devices may each comprise an emitter of UV-C radiation having a wavelength of between 100 and 280 nanometres, providing a high degree of germicidal sterilisation of the exposed outer surface of the passive valve.

Each light emitting device may comprise a light emitting diode that emits UV light. These may be fixed to the surround of the UV emitter. They may be mounted on one or more printed circuit boards.

Alternatively, rather than using LEDs, the light emitting devices may comprise fibre optical cables the conduct light from a remote source to the region of the void. In this case the light may be generated by a light source such as an LED, a laser diode, a laser of any other suitable source.

The UV sterilisation device may include one or more further light emitting devices that emit UV-C light that are located at a position that is on the opposite side of the active valve to the void to expose the underside of the active valve when the active valve is closed.

The UV sterilisation device may include a controller that controls the operation of the UV emitter devices. This may control the duration of emission of the light to ensure a minimum exposure time required for sterilisation is achieved.

The controller may be located remotely from the emitter assembly. The controller may include any driver circuitry required by the light emitter devices, e.g. LED drivers.

The UV sterilisation device may include an interlock which prevents the UV light source emitting light if the two docking parts are not correctly docked. This ensures that an operator cannot be exposed to harmful UV light by operating the light source when the emitter device is exposed. By correctly docked we mean the passive and active valve assemblies are fixed together to seal the void.

The interlock may comprise an optical interlock which includes a source of infrared light and an infrared detector that is sensitive to the light and exposed to the light when closed and not exposed to the light when open, or vice versa.

The interlock may comprise a mechanical interlock which engages automatically when the docking parts are correctly docked.

The docking part of the active valve may comprise an upper body and a lower body, the lower body being fixed to a spigot, and the upper body slidably supporting the active valve, and a clamping mechanism that moves the upper body from a first position towards a second position where it is closer to the lower body when the active valve is fully open to cause the spigot to pass through the opening that would be occupied by the active valve if it was closed.

The complimentary docking part of the passive valve may be fixed to the upper body of the active valve assembly in two positions. In a raised position it may be fixed so that there is a void between the outer face of the passive valve and the other face of the active valve. In a lowered position, the passive valve may engage the active valve so that they may both be slid open in a single action.

The upper body of the active docking part may include a slot through which the active part can be withdrawn and through which the passive valve may also be withdrawn when the passive docking part is lowered. The active valve may include a handle that enables it to be opened and closed. Movement of the active valve may cause corresponding movement of the passive valve.

The passive valve may sit within a recess formed in the upper surface of the active valve when lowered.

The two docking parts may be arranged such that the end of the spigot, when the valves are both open and the spigot is raised, will form a seal with the docking part of the passive valves assembly.

The UV emitter may be an integral part of the upper body of the active docking part. Light emitters may be spaced around a circumference of a through opening of the docking part that the spigot passes through and that is closed by the active valve.

The UV emitter may be configured so that in use the end face of the spigot that has passed through the active slide valve will be exposed to UV light from the UV emitter. The spigot may pass through the UV emitter to contact part of the passive valve assembly during discharge of material. In this position the spigot may form a seal with the docking part of the passive valve assembly that is located such that is prevents material being transferred through the valves from contacting the UV emitters.

The coupler assembly may be configured so that the passive valve cannot be opened independently until it is connected and preferably locked onto the active valve. This prevents material passing from the container until the active valve is open.

The coupler assembly may be so arranged that in its second position the spigot extends through the active valve only, or through both the active valve and passive valves. In the latter case it may protect them both from exposure to material flowing through the valves.

The spigot may comprise a tube having a first end and a second end, and in the second position of the upper body of the active docking part the second end of the spigot passes through the active valve assembly but in the first position does not pass through. In the second position the first end of the spigot preferably forms a seal with a part of the passive valve assembly to substantially prevent the passage of material flowing through the passive valve contacting any part of the active valve. It most preferably forms a seal with the side of the passive valve assembly facing the active valve. This is preferred because, in most cases, where the passive valve provides a closure to a bag or other container of powdered material, this side will be on the outside and so will be free of powder.

The passive valve assembly may include an internal shoulder against which the first end of the spigot abuts when pushed or pressed through the active valve. The second end of the spigot may form an interference fit with the shoulder or with an inwardly directed ring adjacent the shoulder. This fit ensures material is substantially prevented from contaminating either of the valve assemblies.

The shoulder and end of the docking part may be sterilised in use by the UV sterilisation device.

The active valve part and the passive valve parts may be completely detachable, the active valve normally being fixed in place and the passive valve fixed to a flexible bag or a bottle or other type of container which can be moved around.

Of course, the active part may be the part fixed to a flexible bag or other container and the passive part may be fixed in position as part of a process plant or such like.

The spigot may comprise an integral part of the active valve assembly, and may be supported relative to the active valve by a suitable mechanism which enables the required movement of the first end of the spigot into the active valve once the active valve is opened.

The mechanism may include a lever or handle which enables an operator to cause movement of the mechanism between its first and second positions, and hence provide the required relative movement between the spigot and the active and, where appropriate, the passive valve or valves.

The system may include one or more actuators which are arranged to move the passive and active valves automatically following a predefined, or user controlled/definable, sequence. This allows the whole process, from locking of the interlock upon docking of the bag through sterilising to final closing of the valves and release of the interlock, to be automated.

The actuators may be controlled by the controller of the sterilisation device, or by a further stand alone controller.

A flexible seal may be provided which is fixed to or forms part of the spigot. The seal may connect an end of the spigot to the side of the valve opposite the docking part, the seal preventing passage of material from within the spigot between the end of the spigot and the side of the valve opposite the docking part. This seal may, for instance, comprise a bellows which is fixed at one end to the spigot some distance from the tip of the first end and also to the side of the active valve opposite the docking part. Alternatively the seal may comprise a ring of compressible material that is located around the spigot towards the free end such that when the spigot is moved into its second position within the active valve the seal engages the passive valve part and may be compressed against the active valve to enhance the seal.

The active valve may comprise a slide valve comprising a valve body having an inlet port and an outlet port connected by a passage, the ports being selectively isolated from one another by a movable valve plate which is supported in guide slots located between the inlet and outlet port or on rollers and in which the valve plate is free to move between a closed position in which it blocks off the passage and an open position in which it unblocks at least part, and preferably all, of the passage When closed no powder can flow from the inlet to the outlet through the passage, but when open the powder can flow through the passage within the spigot that is located within the valve passage to protect the valve passage. This way the material may be restrained from contaminating the valve plate, or any part of the valve passage.

The passive valve may similarly comprise a slide valve with a valve plate that closes off a passage, and again when in the second position the spigot may protect this passage. In particular, the spigot may protect the exposed slider voids, which are left when the active or passive slides are retracted. Indeed, the spigot may prevent the contents of the container coming into contact with any part of the valves, including the slider voids.

The valve plates of both valves may be secured together so that they can be moved in unison.

Other types of valve may be provided. For instance one or both of the valve assemblies may each comprise an iris valve in which the throttle comprises a tube of flexible material coupled rigidly at each end to a respective one of two flanges, one flange forming the input port and the other flange the output port, the two flanges being free to rotate relative to one another to twist the tube of flexible material thereby to block flow through the valve assembly or to untwist the tube to allow flow of powder or to allow insertion of the first end of the spigot as appropriate. Alternatively, butterfly valves may be provided.

A handle may be provided which enables an operator to open and close the active valve, and at the same time the passive valve. The handle may be part of the active valve.

The spigot may be substantially rigid and solid walled so no material flowing through it can escape through the spigot walls to contaminate the valves. It may for example be a tube, which may be cylindrical. The external diameter of the spigot may be smaller than the internal diameter of the active valve over at least the first end portion which passes though the active valve.

One of the docking parts of the coupler assembly may comprise a recess into which the other docking part may be located by a snap fit. The recess may form part of the active valve part.

A lip may be provided around a perimeter of the recess and a groove may be provided on a perimeter of the passive valve part which engages the groove. Alternatively the lip may be provided on the passive valve and may snap into a groove on the active valve.

The passive valve assembly may be secured to a container such as a flexible bag or a bottle having a body and an outlet. A clamp, or other additional valve such as a butterfly valve, may be provided as part of, or attached to the bag or bottle, between the body of the bag which holds the material to be discharged and the coupler assembly to isolate the coupler assembly from the material until the clamp or valve is opened. This clamp or valve helps prevent the content of the bag contaminating the coupler assembly.

In a preferred arrangement the container is a bag with a flexible neck and the clamp clamps the neck shut. The clamp or other valve should, of course, be releasable or openable at the time the material is to be discharged, i.e. after the transfer assembly has been fixed to the docking station, the valves opened and the spigot pressed through the valves to restrict contact of the material with the valves.

The main body of the bag may contain the material to be discharged.

The bag may comprise an intermediate bulk container (IBC).

The active valve or each active valve of a double active valve coupler assembly may be connected to a respective container or to materials processing equipment or to a pipe that may feed into processing equipment or a container.

A seal may be provided at the first end of the spigot. It may be located at least partially within a groove in an end face of the spigot. It may comprise a substantially rigid ring which is located in the groove with an over-moulded ring of softer material. The rigid ring ensures that the softer ring does not "roll off" the end face of the spigot. An additional seal may be provided on the passive valve which may engage the sliding valve part. This may again comprise a rigid part received at least partially in a groove and a softer over-moulded part. The seal prevents material escaping between the sliding valve part and the fixed part of the passive valve assembly.

The UV sterilization device may be releasable from the passive and active valve parts.

Therefore, according to a second aspect the invention provides a UV sterilization device suitable for sterilising the docking parts of a transfer system of the kind which comprises an active valve assembly having an active valve and docking part suitable for docking to a passive valve assembly which comprises a passive valve and a complimentary docking part, the two docking parts in use enabling the two assemblies to be secured together in a first position such that both the passive valve and active valve face each other across a void but cannot be opened to provide a passage for powder through both valves, and characterised in that the sterilisation device includes a UV light emitter capable of emitting UV-C light which is located such that in use of the sterilisation device the void and the facing surfaces of the passive valve and the active valve are exposed to UV-C light emitted by the emitter assembly.

The UV sterilisation device may be integrated into an active valve assembly or into a passive valve assembly.

The UV-C sterilisation device may comprise a support body having a through hole, the UV-C light emitter comprising a plurality of light sources spaced around the hole.

The light sources may comprise LED's.

According to a third aspect the invention provides a method of discharging materials from a container using the system of the first aspect of the invention comprising:

(a) docking a container fitted with a clamp and a closed passive valve assembly to a closed active valve assembly such that the two closed valves face each other across a void, (b) prior to opening the active valve and the passive valve and after docking step (a) exposing the void and thereby the facing surfaces of the active valve and the passive valve to UV-C radiation to sterilise the surfaces, (c) opening the active and passive valves, and (d) transferring at least some of the contents of the container through the coupler assembly.

Between Step (b) and step (c) there may be a step comprising moving the facing surfaces of two valves towards each other to close the void prior to opening the valves in a combined action. After this step the passive valve and active valve may be interengaged so they can only be opened or closed together.

The method steps (a) to (d) may be carried out in alphabetical order as listed.

Where the apparatus of the first aspect includes a spigot the method may comprise an additional step between opening both the active valve assembly and the passive valve and the step of transferring contents of the container comprising sterilising the spigot.

Following the step of sterilising the spigot the method may comprise bringing the spigot through the active valve to engage the docking part of the passive valve.

There now follows, by way of example two embodiments of the invention, described with reference to the accompanying drawings, in which:

FIGS. 1a, 1b, 1c and 1d show a passive slide valve of a coupler assembly in four views, the valve is shown closed in 2c and open in 2d;

Figure 3:
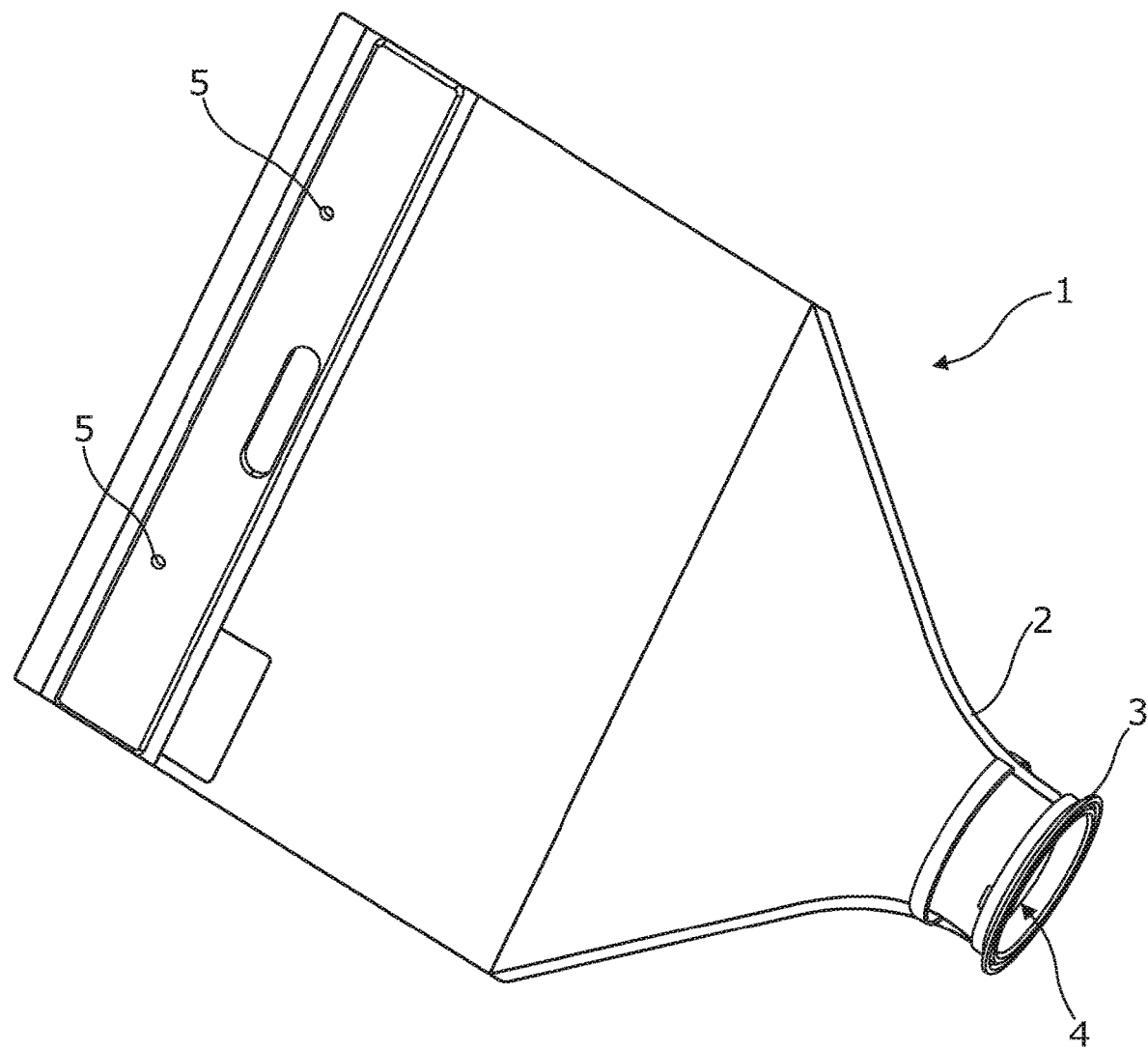
FIG. 3 shows a charge bag which is well known in the pharmaceutical industry for containing powder.
Figure 4:
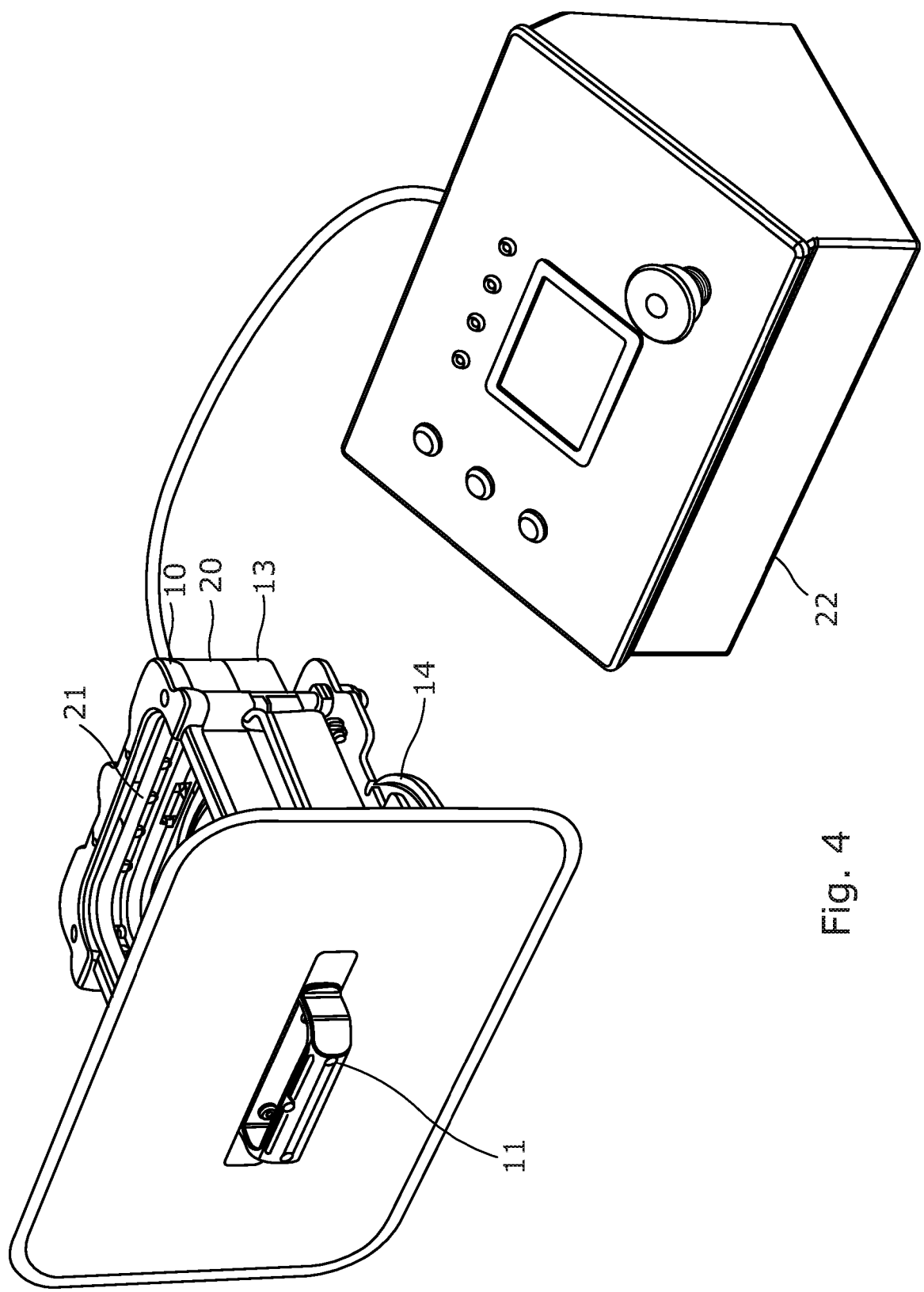
FIG. 4 shows the location of the UV emitter assembly on an active valve part of an embodiment of a connector assembly of the present invention.

FIG. 3 shows an example of a typical container 1 for the transport and containment of materials such as those in powder form used in the biotechnology and pharmaceutical industry. Such containers are well known, and are sold under the name "charge bag". They comprises a flexible polythene bag with a funnelled neck 2 onto which a docking ring 3 is mechanically fastened (see GB2412652 for further details) to form an opening 4. The ring forms half of a seal between the bag and the input of a powder processing unit. The bag can be suspended from the holes 5 on the top of the bag so powder in the bag moves down the neck and out through the opening 4 under gravity. The top of the bag containing the holes 5 are separately sealed from the main volume which contains the powder. Charge bags are disposable and may be incinerated after use.

FIGS. 5 to 16 shows a first embodiment of a contained transfer system including a coupler assembly 6 that is in accordance with an aspect of the present invention. The system comprises three main parts:

A passive valve assembly;

An active valve assembly; and

A UV sterilisation device that in this example is integral to the active valve assembly and includes a remotely located control unit.

The coupler assembly 6 allows the powder material in a charge bag or other container to be safely connected to and transferred into the input of a powder processing unit without powder escaping to the external environment. Other coupler assemblies may be provided in accordance with the invention, for example omitting the spigot. The slide valves may be substituted by butterfly valves.

The passive slide valve assembly 7 of this embodiment is shown in more detail in FIGS. 1*a* to 1*d*. The valve itself comprises a slideably moveable plate 7*a* that is located between two guide rails 7*b*, 7*c* in a passive docking part 8. The docking part has a central hole 7*d* which is covered by the plate 7*a* when in a closed position and which is uncovered as the plate in moved to the open position. A coupler ring 8*a* is formed into an upper face of the docking part 11 which can be secured to the corresponding ring 3 fixed to the end of the charge bag.

The passive valve 7 is made from plastic materials such as nylon or High Density Polyethylene (HDPE) and is a low cost part which may be disposed of with the used charge bag. The passive slide valve provides containment of any powder residues remaining within the bag which otherwise may escape to the external environment when exchanging charge bags.

The active valve assembly 9 comprises a docking part formed as two bodies. One of the bodies defines an upper body 10 which slidably supports a plate 8*a* that forms the active valve and also provides a connection to the docking part of the passive valve assembly when docked. The slider or plate 8*a* defines an active valve which can be opened by sliding through a slot in the side wall of the active part by drawing on a handle 11 in a direction parallel to the plane of the plate.

The upper surface of the plate 8*a*, by which we mean the surface that faces towards the charge bag in use, includes a recess for receiving the passive valve plate 7*a*. When in the recess, the withdrawal of the active valve plate 8*a* will also cause the passive valve plate 7*a* to be withdrawn.

The active slide valve 8 opens and seals a passage through the upper docking body 10 defined by a hole 12 in the upper docking body.

The second body 13 of the active docking part is located below the upper body 10 defines a support for a spigot 14 and a mechanism 13 which vertically raises and lowers the spigot through the hole 12 in the upper docking body 10. In this example, there is approximately 15 mm of movement between the raised and lowered positions of the upper body relative to the spigot 14 which is fixed in position beneath by the lower second body 13. Note that this movement is only possible with the valve plates 7*a*, 8*a* slid fully open.

The spigot 14 of this embodiment is a round tube that protects the internal walls of the passive and active valves from exposure to powder that flows through the coupler assembly. The spigot 14 is always fully contained and never exposed to the external environment. When the active part is lowered, the spigot 14 moves through the passive and active valves covering their internal walls and protecting them from exposure to the powder. This ensures the walls of the valves remain clean so that when a charge bag is replaced and the passive and active valves are separated, no powder is left on their walls which could escape.

To secure the docking parts together the system includes a clamp mechanism that has two positions. In a raised position, the passive docking part is fixed to the upper body of the active docking part with a void formed between the facing surfaces of the closed valve plates 7*a*, 8*a*. In a lowered position, the passive valve plate 7*a* is dropped into engagement with the active valve plate 8*a*. In this position, the passive valve plate engages with the active valve plate to prevent relative sliding movement between them.

In addition to the features described above the upper body of the active docking part includes an integral sterilising device 20.

Figure 1A:
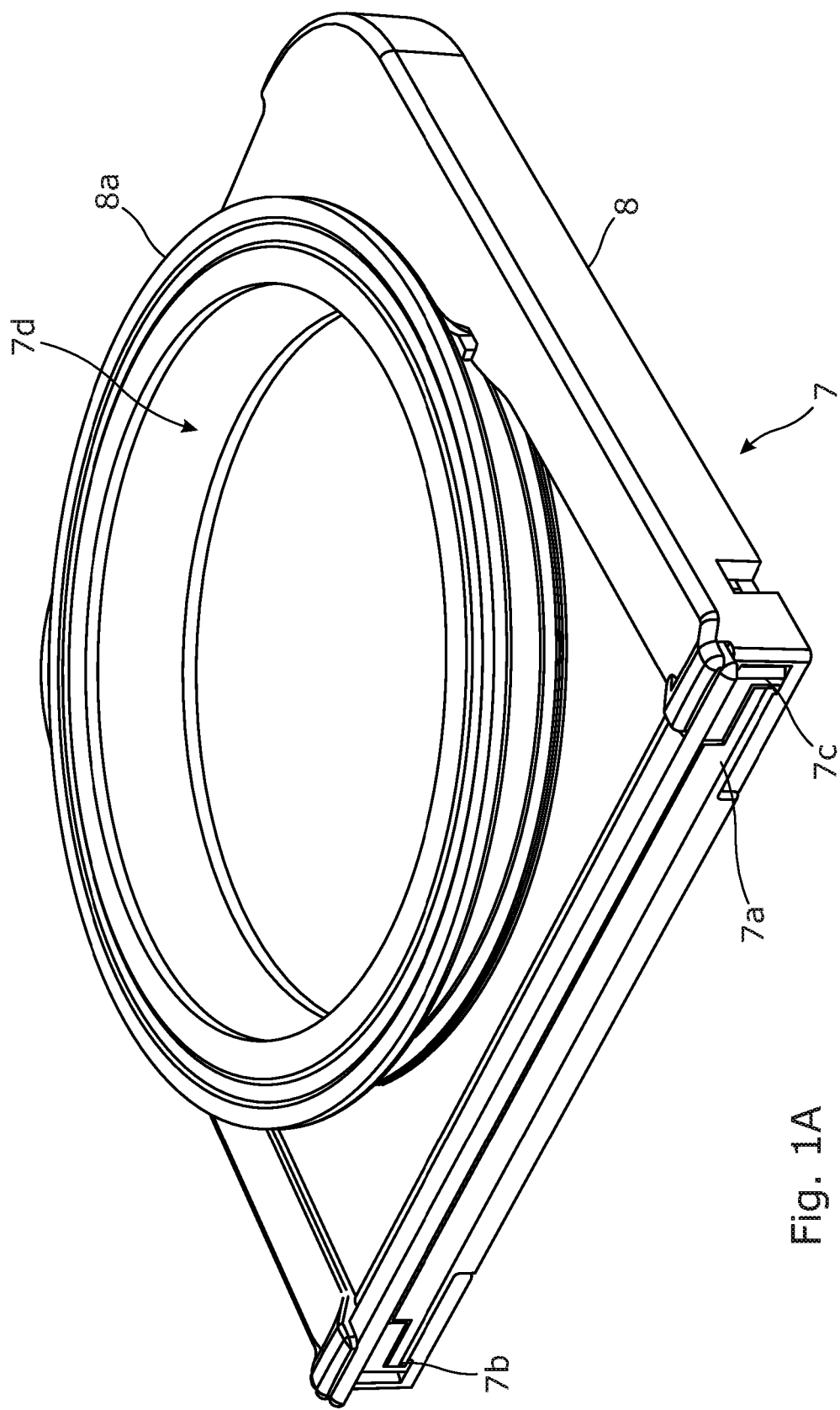
Figure 1B:
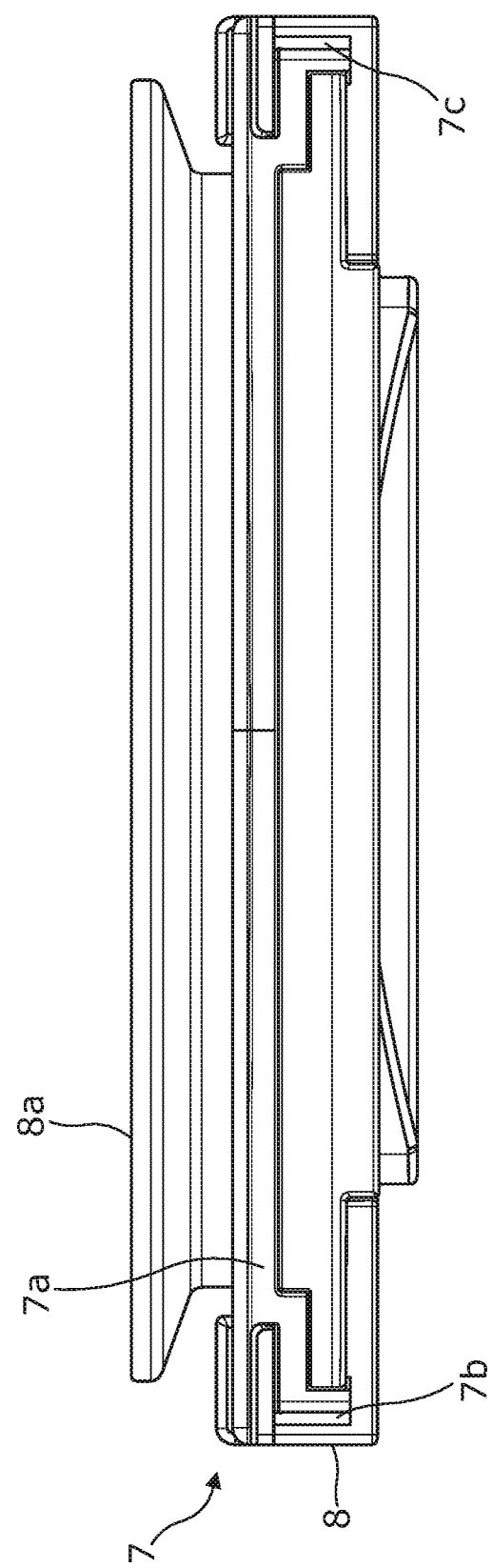
Figure 1C:
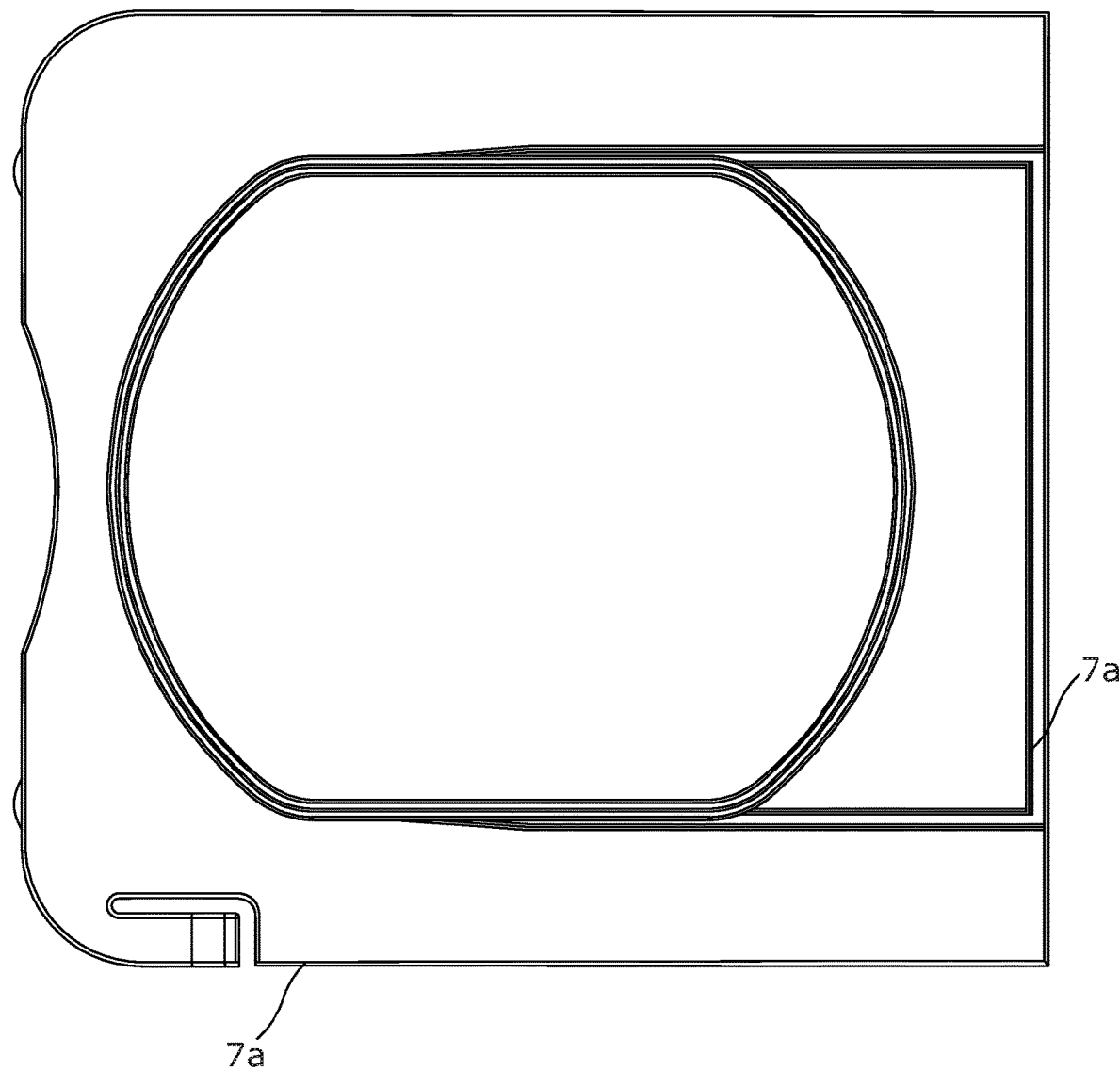
Figure 2:
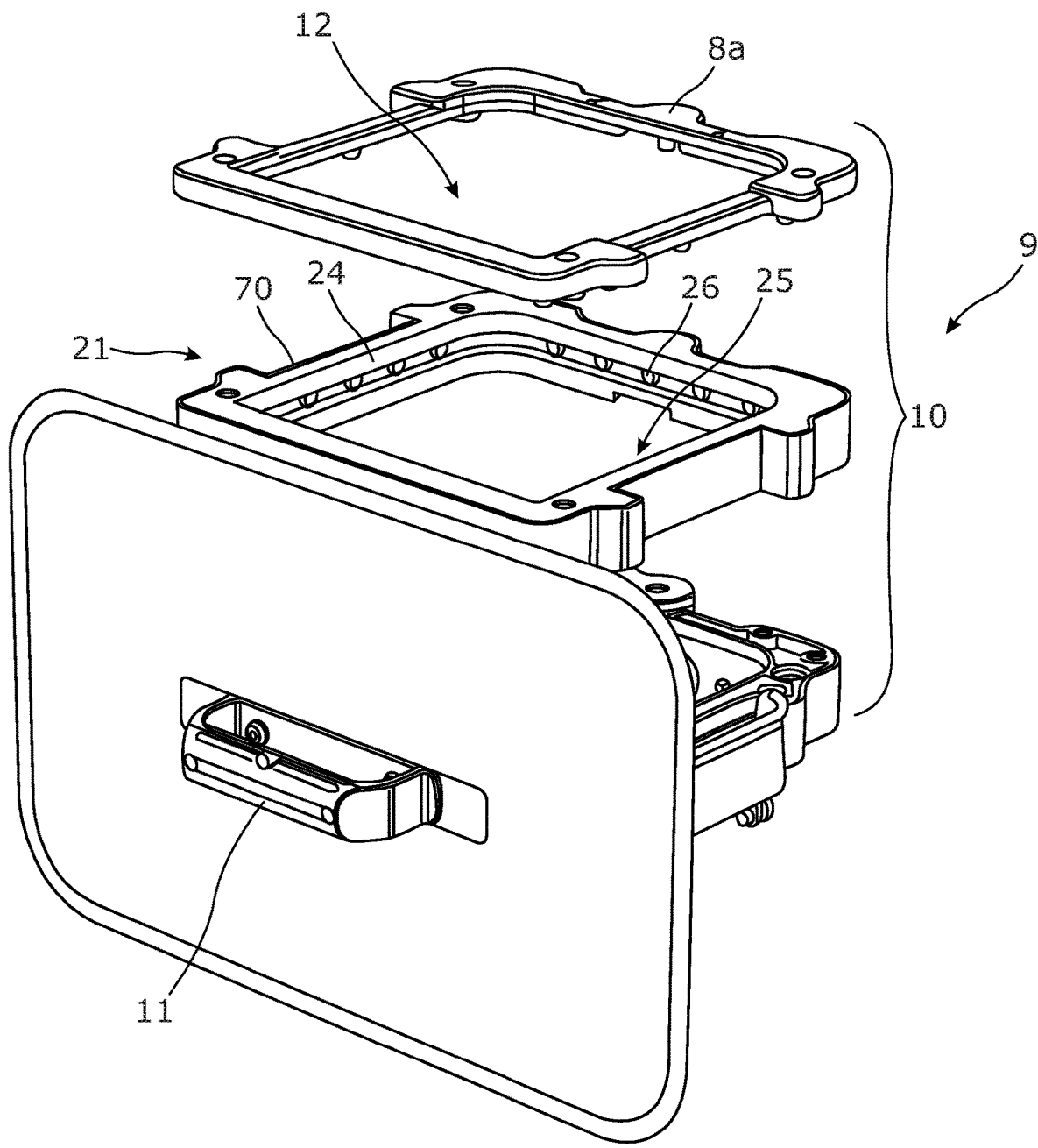
FIG. 2 shows in an exploded view a UV emitter assembly and adjacent active docking valve that forms a part of a sterilisation device that is incorporated into the system in accordance with a first aspect of the invention.
Figure 16:
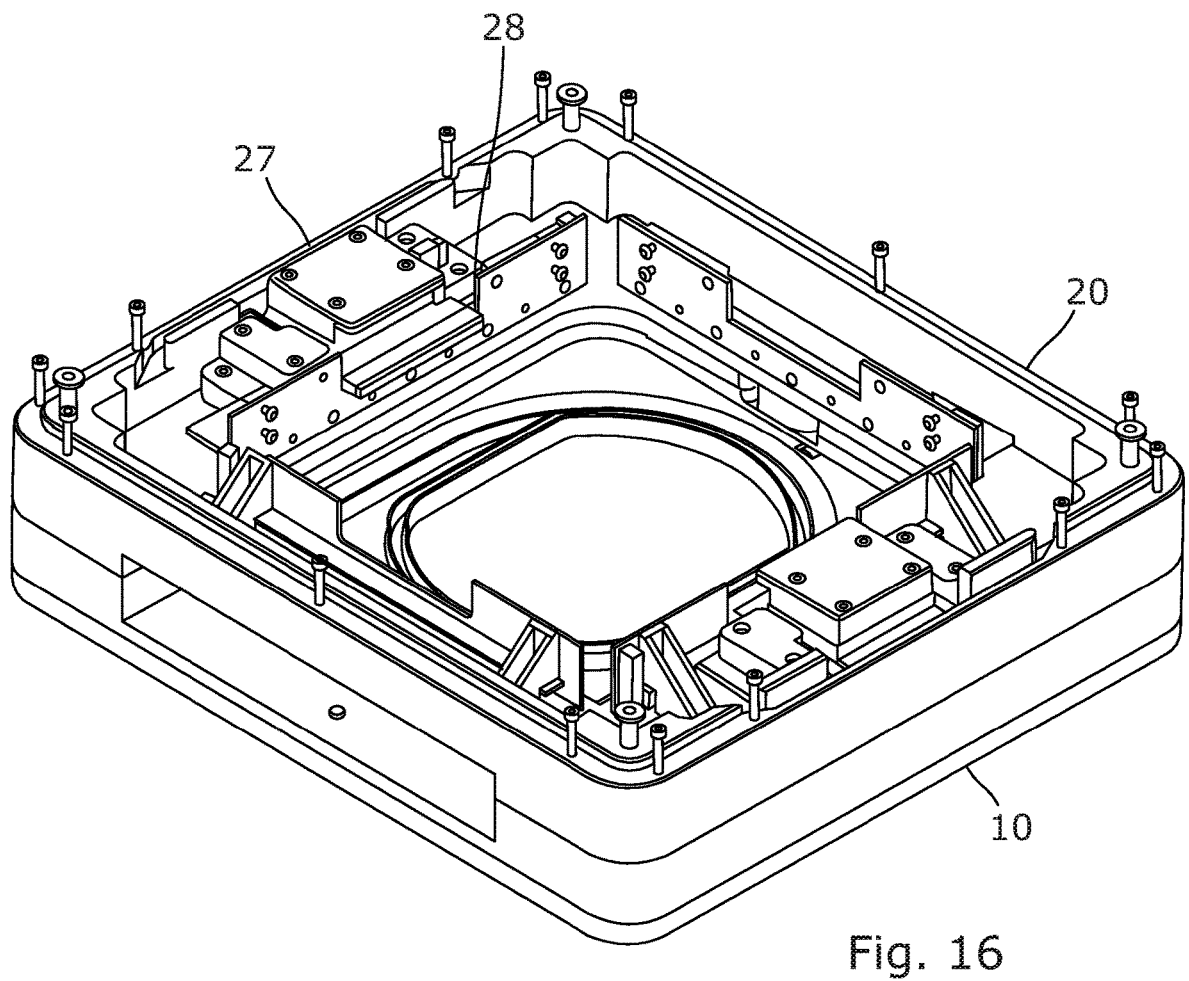
FIG. 16 shows the components of the sterilisation device in more detail highlighting the interlock mechanism.
Figure 17:
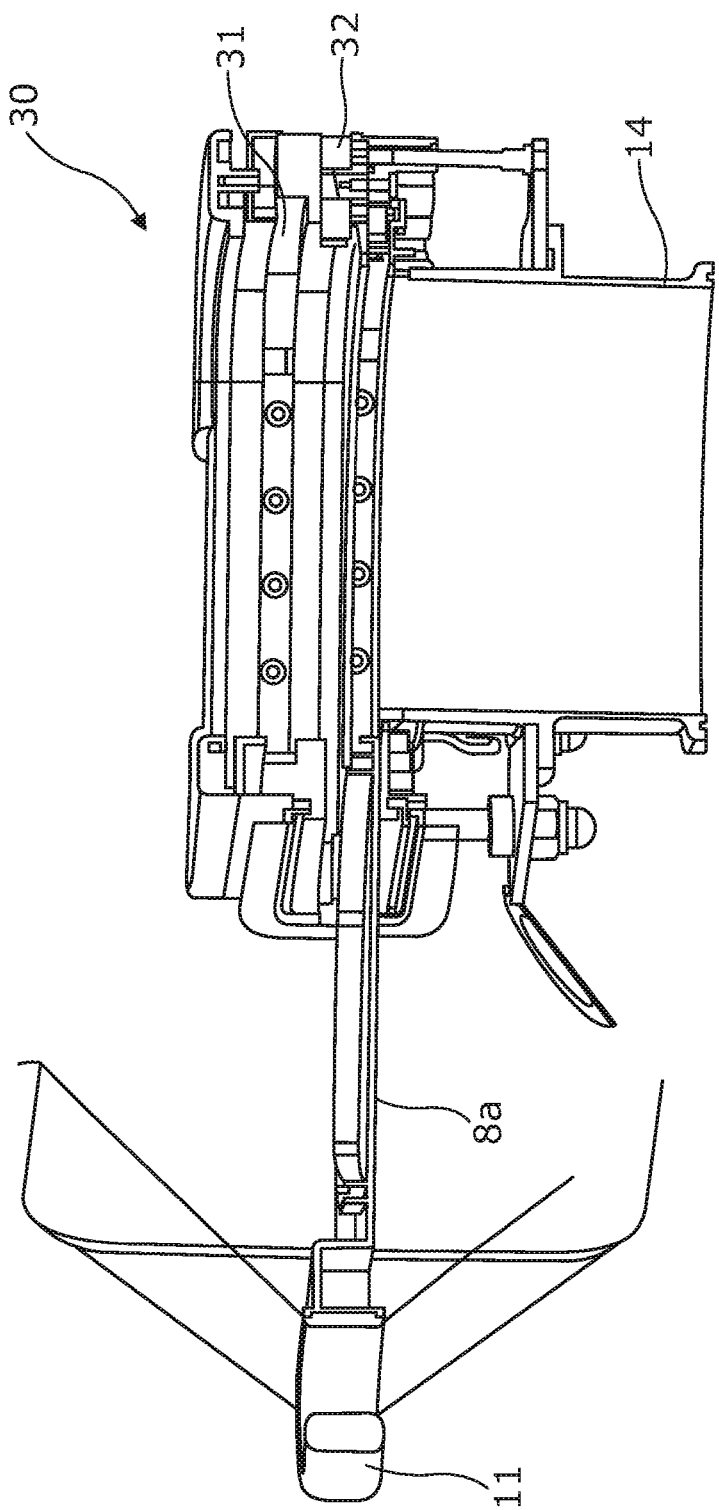
FIG. 17 is an alternative embodiment of an assembly within the scope of the present invention.

The sterilisation device can be seen in exploded form in FIG. 2 and in detail in FIG. 17, and in use in FIGS. 5 to 15 of the drawings, and also schematically in FIG. 16. The device 20 comprises three main components; a UV emitter device 21 that in use is located around the top edge of the active docking part, and a remote controller 22.

The UV emitter device 21 comprises a surround 24 that is pressed fitted into a recess formed in the top of the upper body 10 of the active valve assembly docking part. As shown it has four side walls spaced in opposing pairs to define a central through hole 25. The hole is oversized such that the walls lie adjacent the edge of the hole in the active part upper body. The four walls each carry one of four printed circuit boards, each board carrying a set of five light emitters which each comprises a light emitting diode that emits UV-C light. The LEDs face out across the central through hole.

The surround is positioned such that with the clamp mechanism raised the LED's 26 send light flooding into the void between the two facing surfaces of the passive valve plates 7*a*, 8*a*. It is also positioned such that when the valves are slid open the light will illuminate the end of the spigot before it is raised.

The controller 22 controls the LED light emitters 26. In this example it has a user input in the form of a control button that when pressed causes a light driver 32 to apply a current to the light source 30 to cause it to emit light for a defined period, for example 20 seconds, long enough to sterilise the parts of the connector that are exposed. This time can be pre-set within the controller. The light is coupled to the fibres of the bundle using appropriate optical lenses.

To prevent the LEDs 26 being activated before the active and passive valve assemblies are docked, an interlock 27 is provided, which feeds an electrical signal back to the controller. The interlock as shown in FIG. 17 comprises an electrically actuated solenoid valve having a plunger 28 that engages in a recess in the active and passive valve.

Method of Providing Containment

The system of the described embodiment can be used to sterilise and then transfer material from the charge bag as explained below.

Pre-Stage 1—Docking

The provision of the sterilising device enables the active and passive parts of the coupler assembly to be sterilised prior to discharge of the material in the bag as part of a process of coupling and discharge.

In a first step a passive slide valve 7 should first be coupled to the charge bag 1 with a docking ring 3, as shown in FIG. 3. The powder is initially sealed within the bag by a standard tri-clamp hygiene clamp 18.

The charge bag can then be hung on the discharge frame (not shown) by the holes 5 at the top of the bag.

Figure 5:
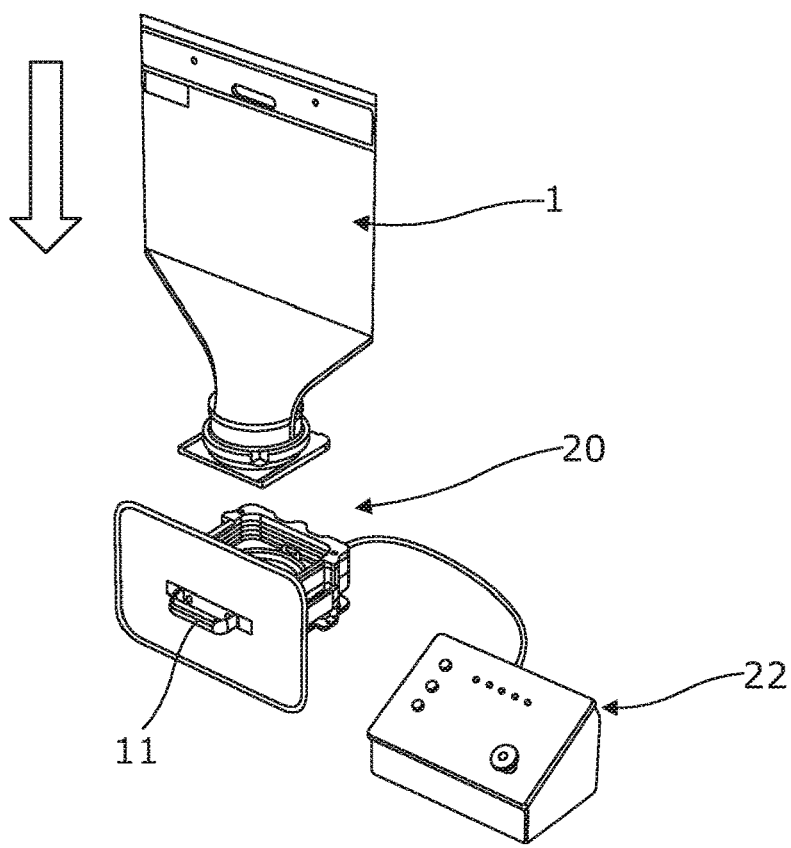
FIG. 5 shows the charge bag with a passive valve part fitted just prior to being docked to the active valve part.
Figure 6:
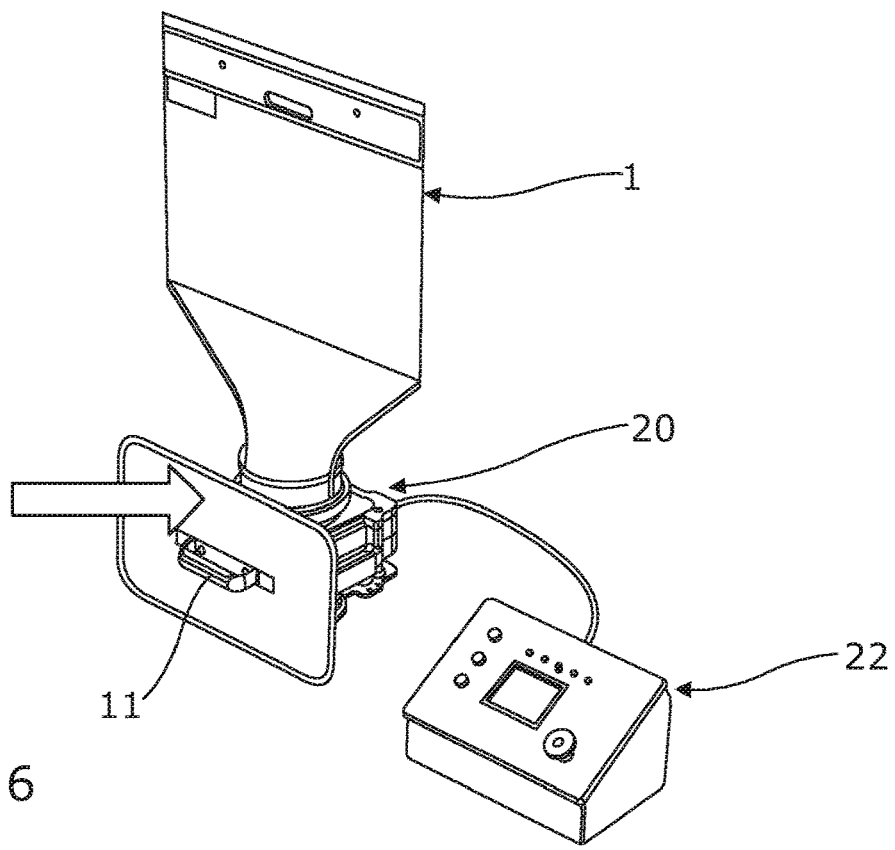
FIG. 6 shows the step of connecting the charge back so the two docking parts are docked and sandwich the UV emitter device.

The passive slide valve can then be clipped onto the active part of the coupler assembly which is supported on the discharge frame as shown in FIG. 5. This forms a closed and sealed volume defined by the active and passive valves which are closed and the walls of the surround of the UV emitter device. The UV sterilisation device is activated and this initially does not emit light but applies the interlock to prevent accidental removal of the bag. This is shown in FIG. 6. The active valve is pushed shut it is was open, as indicated by the bold arrow. The passive valve slide faces but is spaced apart from the active valve slider to define a void.

Stage 1—UV Sterilisation

Figure 7:
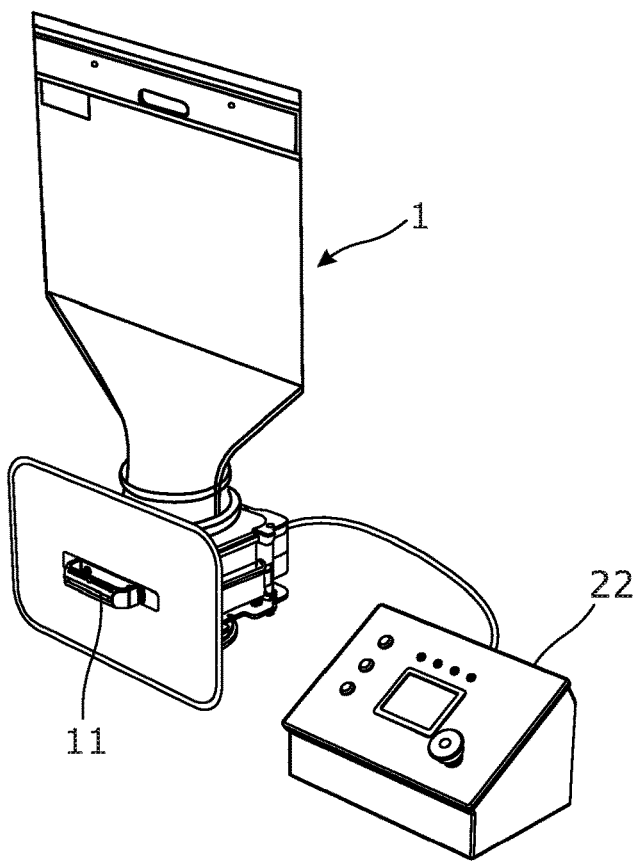
FIG. 7 shows the system of FIG. 5 with the interlock engaged.
Figure 8:
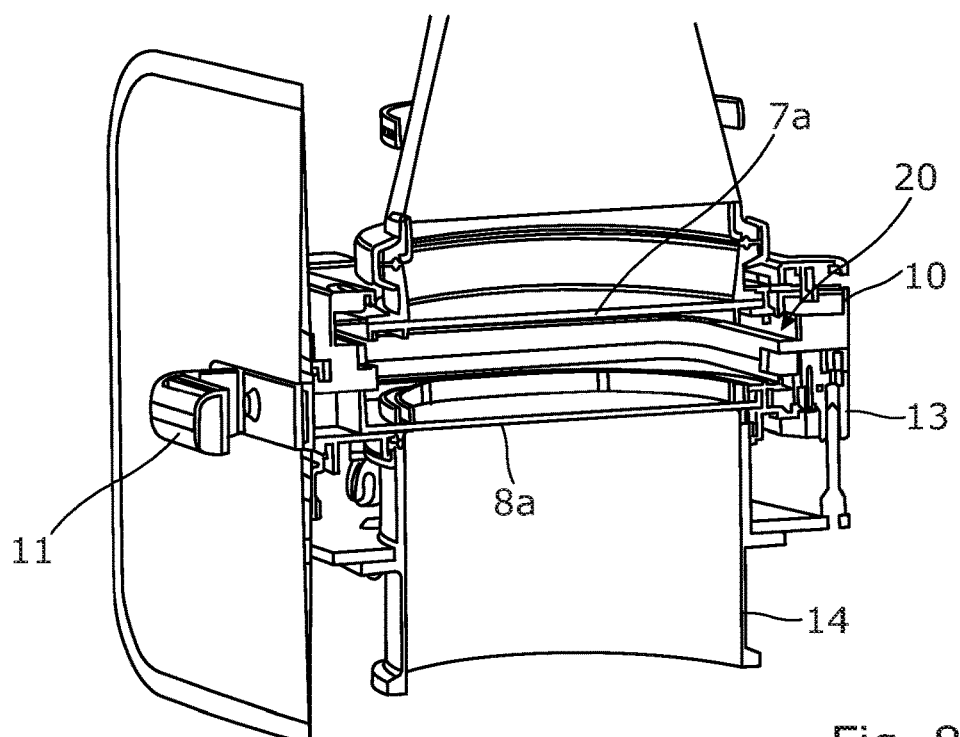
FIG. 8 shows the system in more detail where the light emitters can be seen to emit light onto the lower surface of the closed passive valve prior to opening any of the valves.

In a first cleaning step, shown in FIGS. 7 and 8, the light source is then activated and the UV light emitted by the emitter device sterilises the underside of the passive valve by flooding the enclosed void with UV-C light. This can be seen in FIG. 8 by the light grey shaded area. At the same time the UV-C light bathes the exposed parts of the active valve. This action provides a Stage 1 clean. The areas cleaned are the other faces of the active and passive slide valves, and the immediately surrounding parts.

Stage 2—UV Sterilisation

Figure 9:
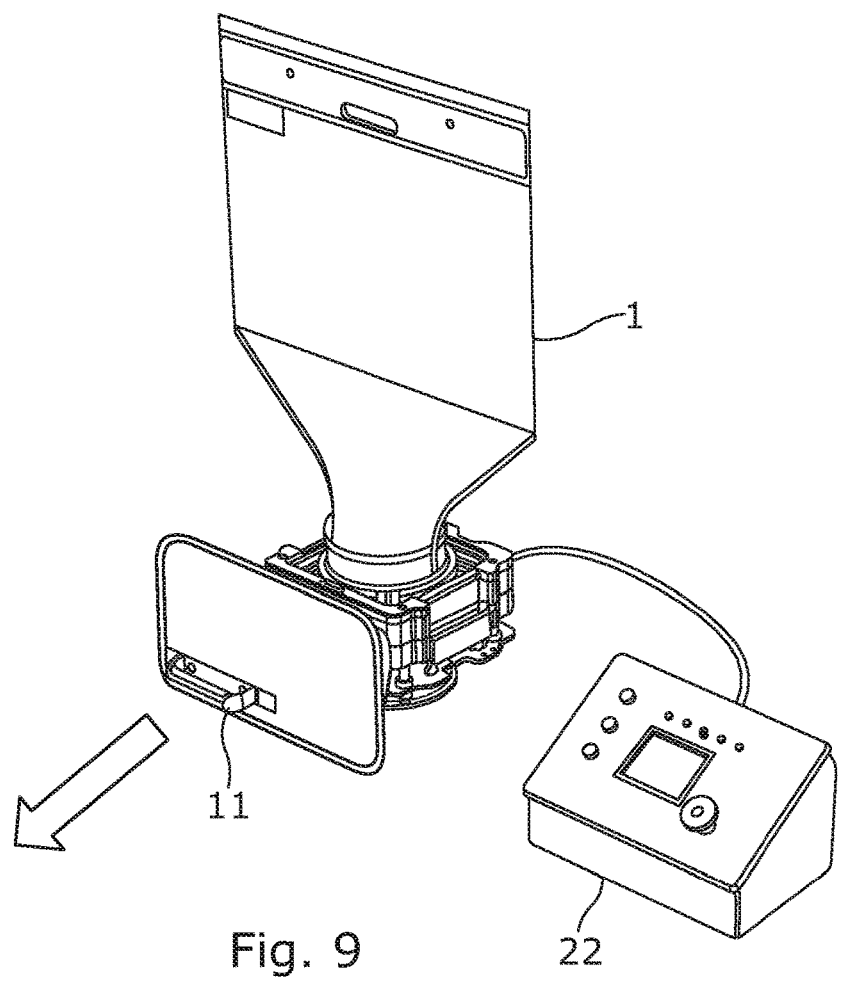
FIG. 9 shows the opening of the active valve in a second stage of cleaning.
Figure 10:
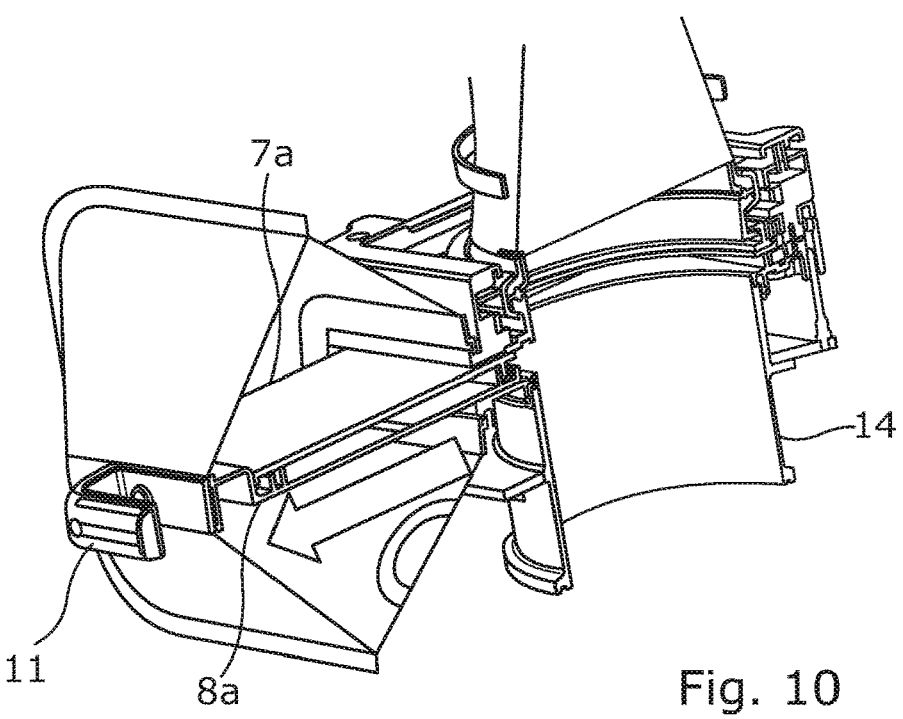
FIG. 10 shows the second stage in more detail with the end of the spigot exposed to the UV light.
Figure 11:
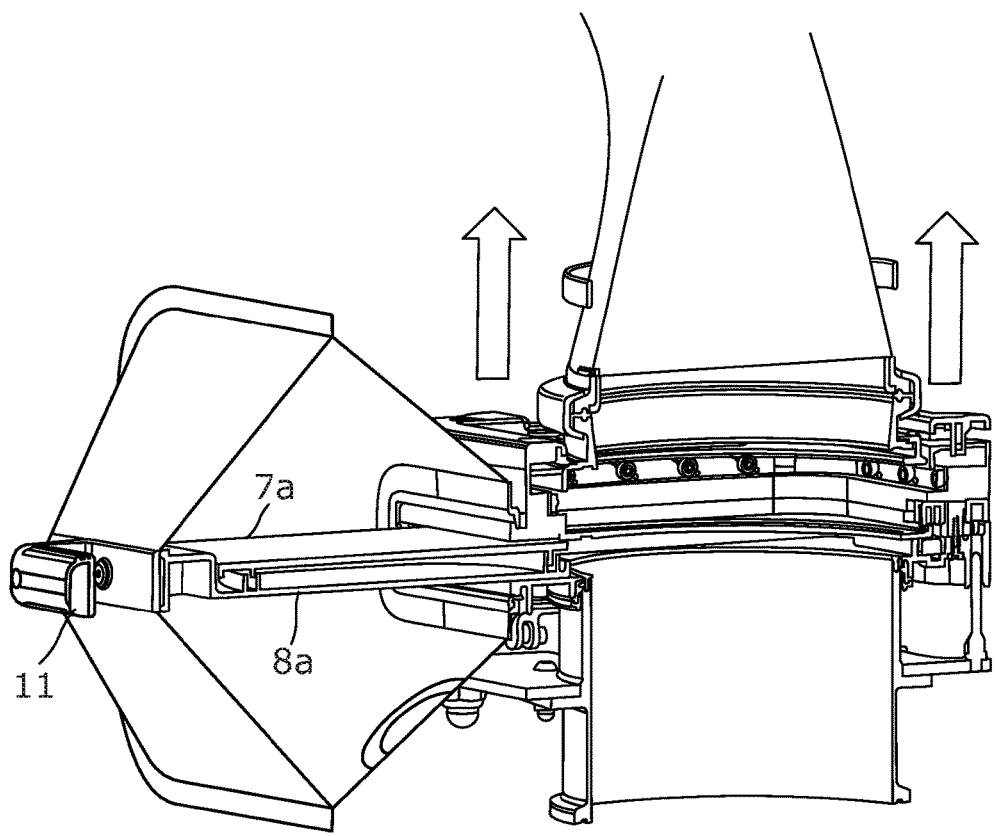
FIGS. 11 and 12 show the passive part being raised to allow the active valve to be opened and then sterilised.
Figure 12:
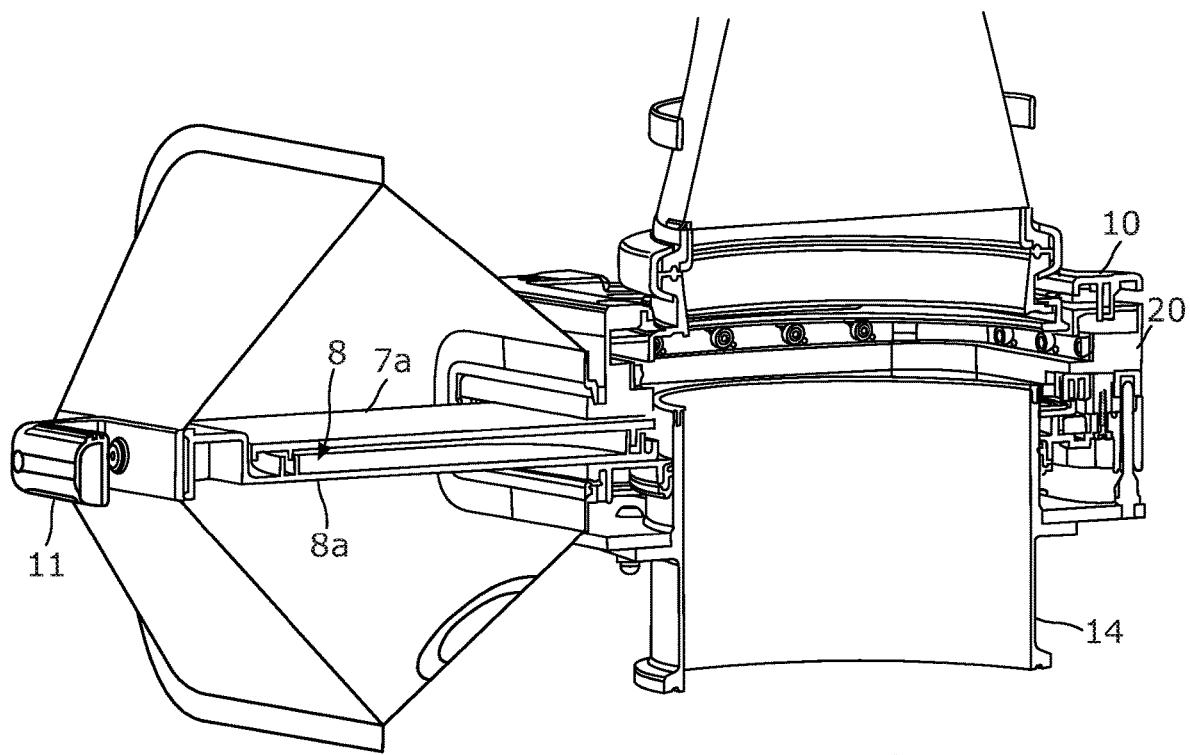

In a next step the active slide valve and passive valves are pushed together by clamping down the passive valve assembly to close the void and are then both slid open in one combined action as shown in FIGS. 9 and 10. At this stage material cannot flow because the bag remains clamped. Opening the two valves exposes the top and inner parts of the spigot into the void that contains the UV LEDs. To ensure the LEDs are not covered by the passive valve part, and to expose the internal faces of the passive valve assembly, the passive valves assembly is then raised up as shown by the bold arrow in FIG. 11. The UV system is again activated as shown in FIGS. 11 and 12. This causes the exposed surfaces of the active spigot and spigot seal to be exposed to the UV light and sterilised. The light is indicated by the light shading in FIG. 12. The UV light source—LEDs 26—can then be deactivated. Also note that the cavity/void left by the removal of the passive/active sliders is also exposed to UV-C light and thus sterilised.

Phase 2—Sealing

Figure 13:
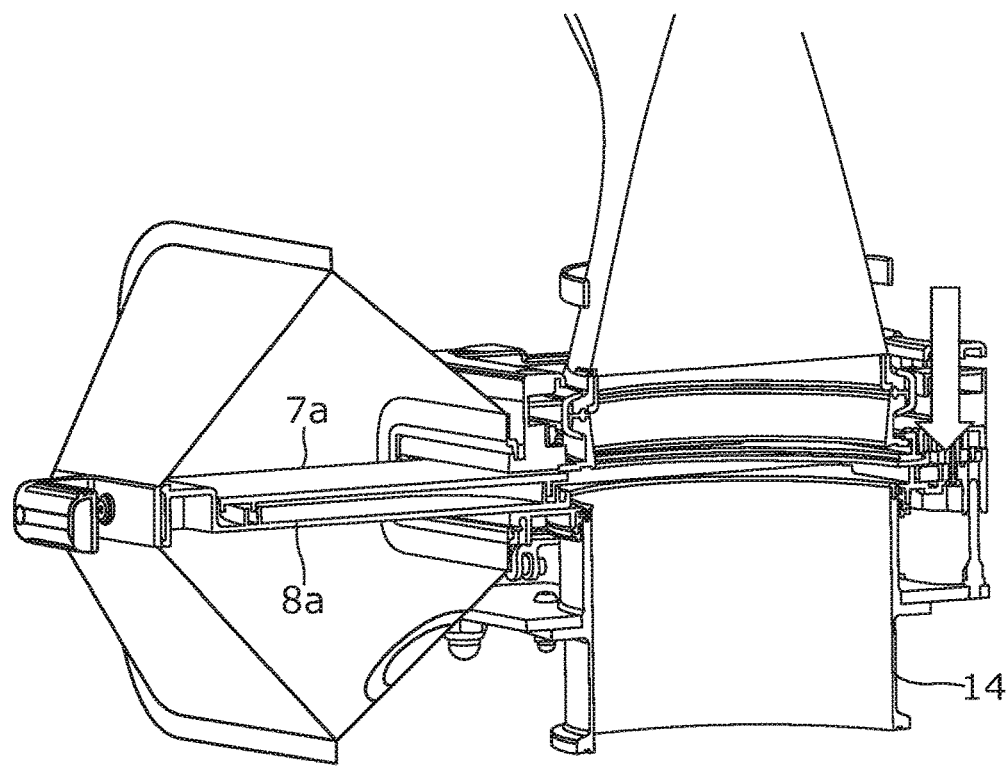
FIGS. 13 and 14 show the passive valve being lowered onto the now closed active valve before both are opened to all transfer of material using the now sterilised coupler.
Figure 14:
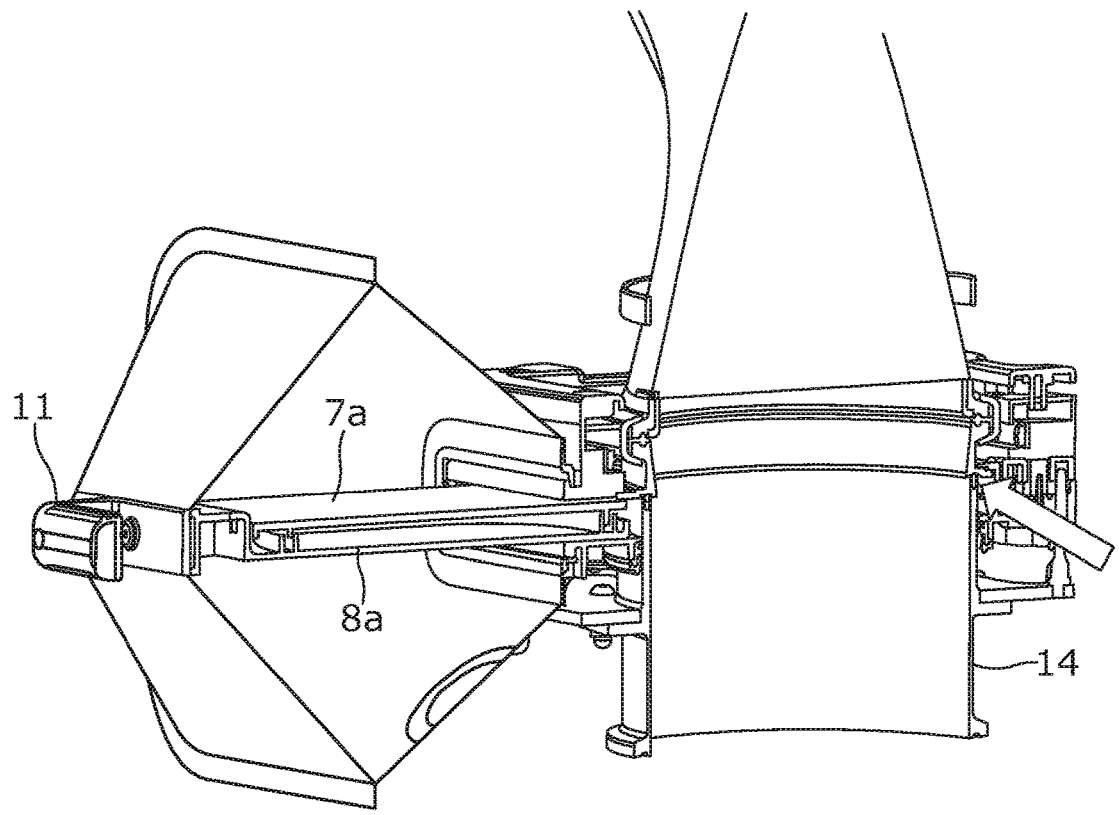
Figure 15:
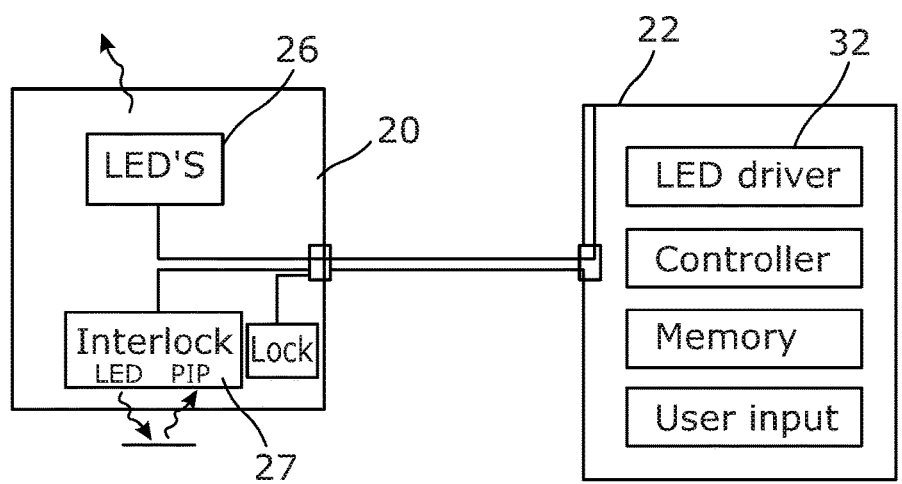
FIG. 15 shows schematically the key parts of the sterilisation device.

In the next step, with both of the valves open, the body of the passive valve assembly is lowered back down into position over the spigot 9 so that the top of the spigot forms a seal to the passive valve body as shown in FIGS. 13 and 14. With the spigot in place the internal walls and exposed slider voids of the 5 valves are protected from exposure to powder and the tri-clamp 18, holding the powder within the charge bag 1, can now be released.

The powder can flow from the bag 1 through the coupler assembly 6 unrestricted to through the spigot. Virtually no powder is wasted by becoming trapped in the couple assembly which would also pose a containment risk.

When the bag is empty the process is reversed, firstly the valves 7, 8 must be raised off the spigot 9.

Undocking

To undock, the sequence above is repeated in reverse order although there is no need to operate the UV-C light emitters as the area is already sterile. The passive valve body is raised from the spigot. The active and passive valves are then closed. The passive valve body is then moved upwards to separate the active and passive side valves. Finally, the passive slide valve is undocked from the active as shown in FIG. 19 with the charge bag 1 remaining attached. The passive slide valve and the charge bag 1 can then be disposed of and the external surfaces of the active valve are left clean to receive another passive slide valve.

A second embodiment 30 is shown in FIG. 17. This is the same as the first embodiment but instead of a single row of LEDs spaced around the body of the sterilisation device there are two rows of LEDs 31, 32, one above the other. The first row is located above the slider 8a of the active valve to sterilise the top of the active slider and the underside of the passive slider 7a. It therefore functions the same as the first embodiment in that the UV light fills the void between the closed active and passive sliders. The second row 32 is located below the slider of the active valve to sterilise the underside of the slider and the top of the spigot. This arrangement allows the sterilisation of the passive and active valves and spigot to be performed in one step if required in stage 2.

The invention claimed is:

1. A system for contained sterile/aseptic transfer of materials comprising:
a coupler assembly including an active valve assembly having an active valve with a valve surface and docking part and a passive valve assembly which comprises a passive valve with a valve surface and a complimentary docking part, the two docking parts enabling the two valve assemblies to be secured together in a first position with a void formed between the two valve surfaces, and
a sterilisation device including a UV emitter assembly arranged in use to emit Ultraviolet (UV) light into the void such that an exposed outer surface of at least the passive valve and active valve are exposed to UV light emitted by the emitter assembly after the two docking parts are secured together in the first position, and prior to moving of the passive/active valve to a second position where material can transfer through the active valve and the passive valve,
and in which the UV emitter assembly includes one or more light emitting devices that emit UV-C light that are located at a position that is on an opposite side of the active valve to the void to expose an underside of the active valve when the active valve is closed.

2. A system according to claim 1 in which the UV emitter assembly is located within, adjacent or at least partially within the void formed by the passive and active docking parts.

3. A system according to claim 1 in which the UV emitter assembly and the docking parts are configured such that when docked and prior to opening the passive valve the passive valve is sealed from an external environment.

4. A system according to claim 1 in which the UV emitter assembly comprises at least one light emitting device that in use emits UV light into the void.

5. A system according to claim 4 in which each light emitting device comprises a light emitting diode that emits UV light.

6. A system according to claim 1 in which the UV emitter assembly includes a controller that controls the operation of the UV emitter assembly.

7. A system according to claim 1 in which the UV emitter assembly includes an interlock which prevents the UV emitter assembly emitting light if the two docking parts are not correctly docked.

8. A system according to claim 1 in which the docking part of the active valve comprises an upper body and a lower body, the lower body being fixed to a spigot, and the upper body slidably supporting the active valve, and a clamping mechanism that moves the upper body from a first position towards a second position where it is closer to the lower body when the active valve is fully open to cause the spigot to pass through the opening that would be occupied by the active valve if it was closed.

9. A system according to claim 8 in which the complimentary docking part of the passive valve can be fixed to the upper body of the active valve assembly in a raised position or a lowered position;
- wherein when the complimentary docking part of the passive valve is fixed in the raised position, there is a void between an outer face of the passive valve and an outer face of the active valve; and
- wherein when the complimentary docking part of the passive valve is fixed in the lowered position, the passive valve engages the active valve such that both can be slid open in a single action.

10. A method of discharging materials from a container of claim 1 comprising:
providing a system of claim 1;
- (a) docking a container fitted with a clamp and a closed passive valve assembly of the system of claim 1 to a closed active valve assembly of the system of claim 1 such that the two closed valves face each other across a void,
- (b) prior to opening the active valve and the passive valve and after docking step (a) exposing the void and thereby the facing surfaces of the active valve and the passive valve to ultraviolet (UV) light to sterilise the surfaces,
- (c) opening the active and passive valves, and
- (d) transferring at least some of the contents of the container through the coupler assembly.

11. A method of discharging materials according to claim 10 comprising between Step (b) and step (c) a step of moving the facing surfaces of two valves towards each other to close the void prior to opening the valves in a combined action, such that the passive valve and active valve are inter-engaged so they can only be opened or closed together.

12. A method of discharging materials according to claim 10 in which the method steps (a) to (d) are carried out in alphabetical order as listed.

13. A Ultraviolet (UV) sterilization device suitable for sterilising the docking parts of a transfer system which comprises an active valve assembly having an active valve and docking part suitable for docking to a passive valve assembly which comprises a passive valve and a complimentary docking part, the two docking parts in use enabling the two assemblies to be secured together in a first position defined by the passive and active valves being in a closed state, wherein the passive valve and active valve face each other across a void in the first position defined by the passive and active valves being in the closed state, the the UV sterilization device including:
- an Ultraviolet (UV) light emitter assembly capable of emitting UV-C light which is located such that in use of the sterilisation device the void and the facing surfaces of the passive valve and the active valve are exposed to UV-C light emitted by the ultraviolet (UV) emitter assembly;
- wherein the UV light emitter assembly includes an interlock which prevents the UV light emitter assembly emitting light if the docking parts of the active valve assembly and the passive valve assembly are not correctly docked.

14. A UV sterilization device according to claim 13 integrated into an active valve assembly or into a passive valve assembly.

15. A system for contained sterile/aseptic transfer of materials comprising:
- a coupler assembly including an active valve assembly having an active valve with a valve surface and docking part and a passive valve assembly which comprises a passive valve with a valve surface and a complimentary docking part, the two docking parts enabling the two valve assemblies to be secured together in a first position with a void formed between the two valve surfaces of the closed valves, and
- a sterilisation device including a UV emitter assembly arranged in use to emit Ultraviolet (UV) light into the void such that an exposed outer surface of at least the passive valve and active valve are exposed to UV light emitted by the UV emitter assembly after the two docking parts are secured together in the first position, and prior to moving of the passive/active valve to a second position where material can transfer through the active valve and the passive valve, in which the UV emitter assembly includes an interlock which prevents the UV emitter assembly emitting light if the two docking parts are not correctly docked.

* * * * *